(12) United States Patent
Conder et al.

(10) Patent No.: US 9,307,997 B2
(45) Date of Patent: Apr. 12, 2016

(54) DOUBLE BAFFLE VASCULAR OCCLUDER

(71) Applicant: Cook Medical Technologies LLC, Bloomington, IN (US)

(72) Inventors: Andrew W. Conder, Bloomington, IN (US); David Nowak Marker, Borup (DK); John R. LeBlanc, Bloomington, IN (US); Susan Gall Sahlgren, Copenhagen (DK); Casper Herdahl, Nykoebing Falster (DK)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 0 days.

(21) Appl. No.: 14/458,679

(22) Filed: Aug. 13, 2014

(65) Prior Publication Data

US 2015/0051586 A1    Feb. 19, 2015

(30) Foreign Application Priority Data

Aug. 13, 2013   (GB) .................................. 1314486.0

(51) Int. Cl.
*A61B 17/12*    (2006.01)

(52) U.S. Cl.
CPC ..... *A61B 17/12109* (2013.01); *A61B 17/12031* (2013.01); *A61B 17/12045* (2013.01); *A61B 17/12168* (2013.01); *A61B 17/12172* (2013.01); *A61B 17/12177* (2013.01); *A61B 2017/1205* (2013.01)

(58) Field of Classification Search
CPC ................... A61B 17/12109; A61B 17/12177; A61B 17/12172; A61B 17/12168; A61B 17/12045; A61B 17/12031; A61B 2017/1205

USPC ......... 606/200; 128/887, 897, 899; 623/23.65
See application file for complete search history.

(56) References Cited

U.S. PATENT DOCUMENTS

| 3,334,629 | A | * | 8/1967 | Cohn | ............................. | 606/194 |
| 4,051,848 | A | * | 10/1977 | Levine | ........................... | 604/304 |
| 4,643,184 | A | * | 2/1987 | Mobin-Uddin | ............... | 606/200 |
| 4,662,885 | A | * | 5/1987 | DiPisa, Jr. | .................. | 623/23.68 |

(Continued)

FOREIGN PATENT DOCUMENTS

| CN | 201814605 | 5/2011 |
| CN | 202143640 | 2/2012 |

(Continued)

OTHER PUBLICATIONS

Partial European Search Report for EP 14275162 (Feb. 19, 2015).

(Continued)

*Primary Examiner* — Manuel Mendez
(74) *Attorney, Agent, or Firm* — Brinks Gilson & Lione

(57) ABSTRACT

A vascular occluder includes first and second baffle members which are formed of an expansion device such as a stent across which extends an impermeable membrane. The baffle members are held at a given separation by spacer elements. The separation creates a chamber between the baffle members in which the blood is able to stagnate, thereby creating a second occlusion barrier. One of the baffle members may have an aperture within its membrane for receiving a delivery catheter for delivery of thrombogenic agent into the chamber. The occluder has a given length, thereby making it suitable for implantation in difficult vessel sections and is also able to avoid problems of recanalization of the vessel which can occur with prior art occluders.

15 Claims, 3 Drawing Sheets

(56) References Cited

U.S. PATENT DOCUMENTS

| | | | |
|---|---|---|---|
| 4,705,517 A | | 11/1987 | DiPisa, Jr. |
| 5,284,488 A | | 2/1994 | Sideris |
| 5,669,933 A | * | 9/1997 | Simon et al. .................. 600/200 |
| 5,733,294 A | | 3/1998 | Forber et al. |
| 5,925,062 A | * | 7/1999 | Purdy ........................... 606/200 |
| 6,251,122 B1 | * | 6/2001 | Tsukernik .................... 606/200 |
| 6,258,120 B1 | * | 7/2001 | McKenzie et al. ........... 623/1.36 |
| 6,554,849 B1 | * | 4/2003 | Jones et al. .................. 606/200 |
| 6,652,555 B1 | * | 11/2003 | VanTassel et al. ............ 606/200 |
| 6,783,538 B2 | * | 8/2004 | McGuckin et al. ........... 606/200 |
| 6,855,154 B2 | * | 2/2005 | Abdel-Gawwad ............ 606/200 |
| 6,964,672 B2 | * | 11/2005 | Brady ....................... A61F 2/01 606/200 |
| 7,854,759 B2 | * | 12/2010 | Shirley ............. A61B 17/12022 606/200 |
| 2004/0044364 A1 | | 3/2004 | DeVries et al. |
| 2004/0254589 A1 | | 12/2004 | Darnis et al. |
| 2005/0065547 A1 | | 3/2005 | Marino et al. |
| 2005/0107867 A1 | | 5/2005 | Taheri |
| 2006/0212055 A1 | | 9/2006 | Karabey et al. |
| 2008/0091235 A1 | | 4/2008 | Sirota |
| 2009/0270974 A1 | | 10/2009 | Berez et al. |
| 2010/0030256 A1 | | 2/2010 | Dubrul et al. |
| 2011/0301630 A1 | | 12/2011 | Hendriksen et al. |

FOREIGN PATENT DOCUMENTS

| | | |
|---|---|---|
| DE | 102009058132 A1 | 6/2011 |
| EP | 0882428 A2 | 12/1998 |
| EP | 2524653 | 11/2012 |
| WO | WO 91/15155 | 10/1991 |
| WO | WO 03/068306 A1 | 8/2003 |
| WO | WO 2005/074844 A1 | 8/2005 |
| WO | WO 2008/115922 | 9/2008 |
| WO | WO 2010/116074 A1 | 10/2010 |
| WO | WO 2012/003317 A1 | 1/2012 |

OTHER PUBLICATIONS

Combined Search and Examination Report for Great Britain Patent Application No. 1314486.0 dated Jan. 31, 2014, 7 pages.
Examination Report for Great Britain Patent Application No. 1314486.0 dated Jun. 3, 2014, 2 pages.
Combined Search and Examination Report for Great Britain Patent Application No. 1411346.8 dated Jul. 31, 2014, 5 pages.
Examination Report for Great Britain Patent Application No. 1411346.8 dated May 20, 2015, 2 pages.
Extended European Search Report for European Application No. 14275162.7 dated Sep. 3, 2015, 12 pages.
Examination Report for Great Britain Patent Application No. 1411346.8 dated Aug. 24, 2015, 2 pages.
Examination Report for Application No. GB1411346.8 dated Jan. 29, 2016, 3 pages.

* cited by examiner

DOUBLE BAFFLE VASCULAR OCCLUDER

CROSS REFERENCE TO RELATED APPLICATIONS

This application is related to and claims the benefit of priority to British patent application number GB 1314486.0, filed Aug. 13, 2013, which is incorporated herein by reference in its entirety.

TECHNICAL FIELD

The present invention relates to a vascular occluder for implantation into a vessel of a human or animal.

BACKGROUND ART

There are several medical indications for which vascular occlusion is an appropriate treatment including, for example, for rerouting blood to a different part of a patient's body, to reduce or halt supply of blood to a tumor or other growth, to reduce the supply of blood to an organ or area of a patient's body prior to a medical procedure or treatment, to reduce pressure on a fistula, weakened or leaking blood vessel, and so on.

Conventionally, vascular occlusion was effected by surgically closing, or ligating, the blood vessel. This required an open surgery procedure with consequential risks and complications.

More recently, vascular occlusion has been effected by the endoluminal implantation into a patient of one or more implantable medical devices. A well-known device is in the form of a wire coil which can be implanted in a patient's vasculature and which achieves occlusion by promoting embolization of blood. Typically, several such coils are implanted one adjacent the other until the medical practitioner is satisfied that adequate occlusion has been achieved. In this regard, it can take time to attain adequate occlusion and also the length of the occluding barrier, that is the overall length of the implanted coils, will vary and can be significant. In some cases, there may not be sufficient room in a vessel to accommodate a long length of coils without adversely affecting other parts of the patient's vasculature, such as side branches bifurcations and so on.

It is also known to effect occlusion by administration of thrombogenic agent into a patient, for instance by injection of the agent between two spaced balloons inflated in a patient's vessel. The balloons are removed following the generation of the blood clot, thereby to create occlusion without leaving in the patient's body any foreign device. The procedure can generate an occluding barrier of set length, thereby making the occlusion barrier suitable for complex vessel anatomies. However, occlusions of this nature can be liable to recanalization; that is, to leakage through the occluding barrier and reopening of the vessel.

Other types of implantable occluders seek to mitigate the above drawbacks but can still be prone to migration, recanalization and migration following implantation.

SUMMARY OF THE INVENTION

The present invention seeks to provide an improved vascular occluder and method of occluding a body vessel.

According to an aspect of the present invention, there is provided a vascular occluder having first and second baffle members. Each baffle member includes an annular expansion device and a membrane extending across the expansion device. One of the first and second baffle members is substantially impermeable and the other of the first and second baffle members is permeable. At least one spacer element is disposed between the first and second baffle members to hold the first and second baffle members at a distance from one another so as to provide a chamber between the first and second baffle members. The first baffle member includes an opening for removably receiving a delivery catheter.

According to another aspect of the present invention, there is provided an assembly for occluding a body vessel. The assembly includes a delivery catheter and a vascular occluder having first and second baffle members. Each baffle member includes an annular expansion device and a membrane extending across the expansion device. One of the first and second baffle members is substantially impermeable and the other of the first and second baffle members is permeable. At least one spacer element is disposed between the first and second baffle members to hold the first and second baffle members at a distance from one another so as to provide a chamber between the first and second baffle members. The first baffle member includes an opening for removably receiving a delivery catheter.

Also described herein is a method of occluding a body vessel including the steps of:

positioning a delivery catheter into a patient, the delivery catheter housing a vascular occluder including first and second baffle members, each baffle member including an annular expansion device and a membrane extending across the expansion device, and at least one spacer element disposed between the first and second baffle members to hold the first and second baffle members at a distance from one another so as to provide a chamber between the first and second baffle members; wherein the first baffle member includes an opening for receiving a delivery catheter;

releasing the vascular occluder from the delivery catheter so as to deploy in a vessel of the patient; and delivering thrombogenic agent through the delivery catheter into the chamber between the first and second baffle members.

The structure and method taught herein provide an occluder which is able to be left indefinitely within a patient, which can avoid the risk of recanalization of the vessel and which in practice can have a reliable length in a patient's vessel, thereby making the device suitable for implantation in locations which have a finite or short length for supporting an implantable medical device. Furthermore, the vascular occluder provides a chamber therewithin able to receive thrombogenic agent, used in causing clotting of blood within the chamber of the occluder and thus an additional and enhanced occluding barrier.

The provision of a plurality of spacer elements gives enhanced stability to the occluder in the vessel and thus optimal occlusion and reduced risk of migration or deformation of the occluder which might otherwise lead to loss of occlusion function.

The following optional and preferred features are applicable to all aspects of the invention disclosed above and elsewhere in this specification.

In an embodiment, the membrane of at least one of the first and second baffle members is substantially impermeable. The provision of a substantially impermeable membrane contributes to substantially immediate occlusion of the vessel without requiring significant time to close off the body vessel.

In another embodiment, the membrane of at least one of the first and second baffle members is permeable. Such a membrane can allow blood to pass into the chamber and then to clot, generating the additional occlusion barrier. Providing a structure and arrangement in which the upstream baffle member is permeable can act to slow the flow of blood into the device and therefore to the downstream baffle member. A reduction of flow of this nature can assist in the formation of thrombi within the device.

Advantageously, each expansion device is a radially expandable ring, for instance a stent ring. Such an expansion device can readily be radially compressed for endovascular introduction into a patient.

It is preferred that each expansion device has rounded outer edges, intended to prevent damage to the vessel wall against which they press in use of the medical device.

The each spacer element may be flexible, for instance being a sprung structure such as a coil spring.

Preferably, the occluder includes anchoring elements provided on at least one of the first and second baffle members. The anchoring elements may be barbs.

Advantageously, the first and second baffle members are radially compressible. More specifically, the entire vascular occluder is preferably configured to be compressible into the delivery catheter.

The delivery catheter is preferably sized to deliver a thrombogenic agent into the chamber between the first and second baffle members.

Other preferred and optional features and aspects will become apparent from the specific description which follows.

BRIEF DESCRIPTION OF THE DRAWINGS

Embodiments of the present invention are described below, by way of example only, with reference to the accompanying drawings, in which.

DESCRIPTION OF THE PREFERRED EMBODIMENTS

Figure 1:
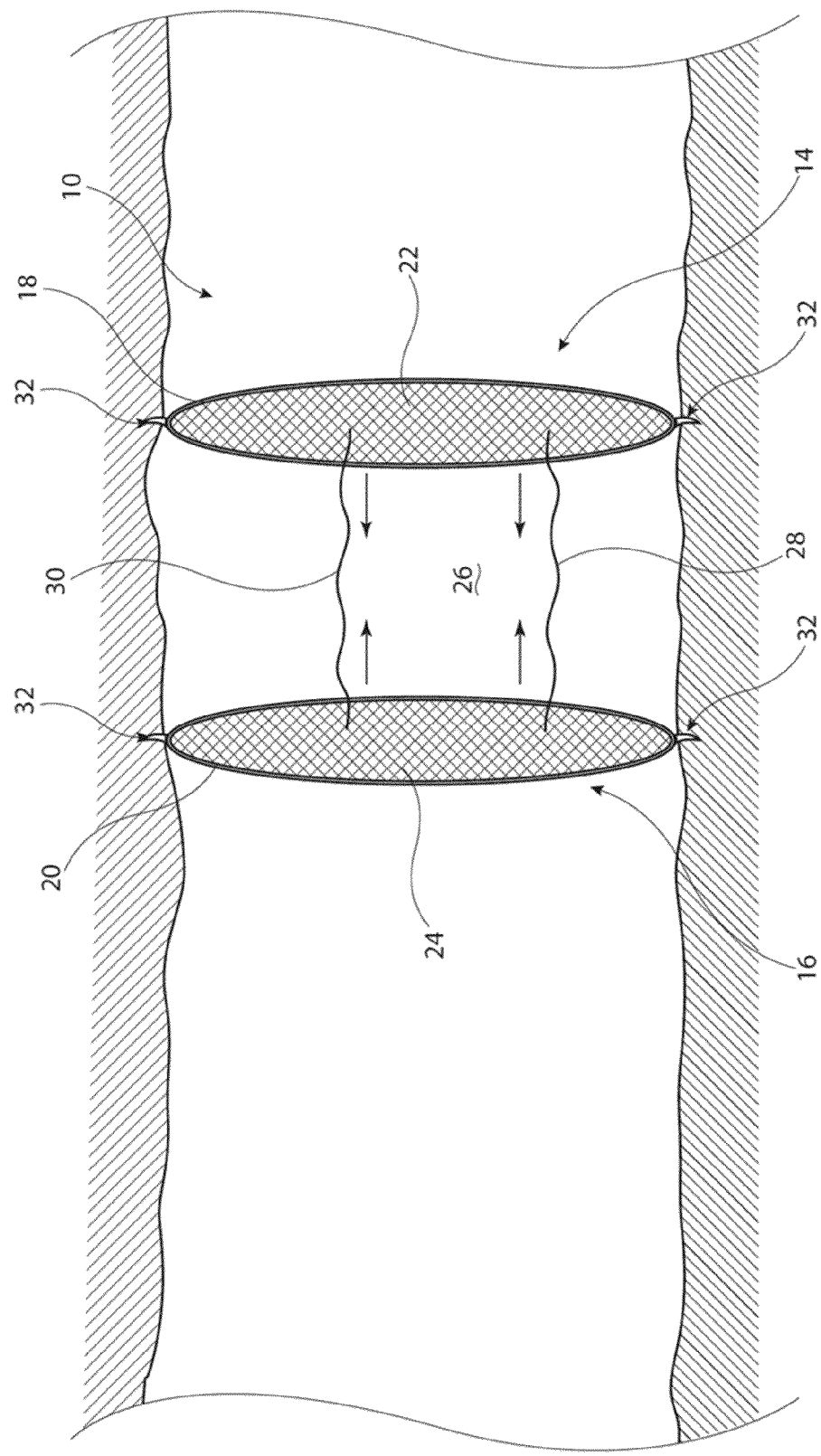
FIG. 1 is a schematic view in side elevation of an embodiment of occluder.

Described below are various embodiments of a vascular occluder for deployment in a patient or animal in order to occlude a body vessel. The structures taught herein are suitable for occluding a wide variety of blood vessels, both of large as well as of small diameter. They are also suitable in high pressure vessels.

The embodiments of occluder described herein include first and second baffle members which in the preferred embodiment have a substantially disk-shaped form and which are coupled to one another by a plurality of spacer elements, which hold the baffle members in position and provide a chamber between the baffle members in which blood therein can clot as a result of blood statis and/or agent activated thrombosis.

It is to be understood that the drawings are schematic only and not to scale. Nevertheless, the skilled person will appreciate the technical elements depicted in the drawings and that these form an integral part of the disclosure of this patent specification.

Referring first to FIG. 1, this shows a first embodiment of occluder 10 disposed within a patient's vessel 12 so as to close off blood supply within the vessel 12. The occluder 10 includes first and second baffle members 14, 16, each of which includes an expansion device 18, 20 and a membrane 22, 24 connected to and extending across its respective expansion device. Each expansion device 18, 20 is preferably annular in shape and may be formed from a stent ring or other compressible annular element. When configured as a stent, each expansion device 18, 20 may be a zigzag stent or other stent known in the art. The expansion devices 18, 20 are preferably of a size that they will expand within the vessel 12 until they abut and press against the internal wall of the vessel 12. For this purpose, the expansion devices 18, 20 preferably have an expanded diameter which is greater than the internal diameter of the vessel 12.

In place of a zigzag stent, the expansion devices 18, 20 could be formed of any other ring structure, for instance one or more turns of a wire arranged as a split ring, or the like.

The expansion devices 18, 20 preferably have rounded external surfaces, in order not to damage the vessel wall. This could be by forming the devices 18, 20 from wire or by rounding any cut lines. Evidently, all surfaces of the devices 18, 20 could be rounded.

The membranes 22, 24 can be attached to the expansion devices 18, 20 by any suitable method including suturing, bonding, by being wrapped around the expansion devices and so on. Preferably, the membranes 22, 24 are complete and unitary across the internal space, or opening, of the expansion devices 18, 20, save for the features described below.

The membranes 22, 24 may be made of woven, knitted or sheet material. They may be made of materials commonly used in the art, such as woven polyester, polyethylene terephthalate such as Dacron, ultrahigh molecular weight polyethylene such as Dyneema, and so on. Similarly, natural materials such as SIS (small intestinal submucosa) and others may be used. SIS or similar material could be in porous sheet form or as woven SIS thread. Another embodiment forms the membranes 22, 24 of woven Nitinol thread.

In one embodiment, one of the membranes 22, 24 is substantially impermeable so as to block the flow of fluid through the occluder substantially instantaneously on deployment of the occluder 10. In such an embodiment, the other membrane 22, 24, is made of a porous material, which would allow blood to flow into the occluder 10, in particular into the space or chamber 26 between the first and second baffle members 14, 16. In practice, the impermeable membrane is positioned downstream relative to the baffle member carrying the permeable membrane, such that blood can flow into the device 10 through the permeable membrane.

In other embodiments, both membranes 22, 24 may be impermeable or porous.

A suitable porous membrane 22, 24 may be formed of the same materials as listed above, but of a weave or knit which is less dense, or of a sheet material provided with apertures or openings therein.

It is preferred that the or each permeable membrane has a porosity such that it will substantially slow the flow of fluid in the vessel and thus contribute to the generation of static blood between the first and second baffle members 14, 16. In an embodiment, each membrane 22, 24 is made from a thrombogenic material, in order to promote blood clotting. This can be achieved with any of the materials mentioned above, and in some instances by providing fibers loosely tied to the membranes which can produce a volume in which blood can stagnate.

The occluder 10 is also provided with a plurality of spacer elements 28, 30 which are connected to the baffle members 14, 16 so as to hold the latter in position and to maintain a spacing between them. FIG. 1 shows only two spacer elements 28, 30. In practice, there will be provided more than two spacer elements, preferably radially arranged around a center point of the baffle members 14, 16 to provide stability to the structure. It is preferred that the spacer elements 28, 30 are spaced from the outer extremities of the baffle members 14, 16, that is the extremities which in practice abut and press against the vessel wall 12. In some embodiments, the spacer elements 28, 30 are spaced roughly at the half-way point between the radial center of each baffle member 14, 16 and its radial periphery. The skilled person will appreciate, though, that the spacer elements may be located at locations other than this center point.

In order to achieve a strong connection between the spacer elements 28, 30 and the baffle members 14, 16, the baffle members 14, 16 may be provided with struts or other frame elements coupled to the annular expansion devices 18, 20 and made of a similar material as the expansion devices.

In other embodiments, the spacer elements 28, 30 may be connected directly to the membranes 22, 24.

The expansion devices 18, 20 and any other frame elements of the baffle members 14, 16 may be made of spring material such as spring steel or the like. It is preferred, though, that the expansion devices 18, 20 and other structural elements of the baffle members, 14, 16 are made of a shape memory material such as a shape memory polymer or alloy. A preferred material is an alloy containing nickel and titanium, such as Nitinol.

The spacer elements 28, 30 are preferably flexible and may also be longitudinally expandable. In this regard, the spacer elements 28, 30 may be made of an expandable material or have an expandable form, such as a coil spring. The spacer elements 28, 30 may be made of the same material as the expansion devices 18, 20.

One or both of the baffle members 14, 16 may be provided with an plurality of barbs 32 extending out from one or both of the expandable elements 18, 20, the barbs 32 acting as anchor elements able to grip into the tissue of the vessel 12 and thereby hold the baffle member or elements 14, 16 in position once the occluder 10 has been deployed in a patient's vessel 12.

Figure 2:
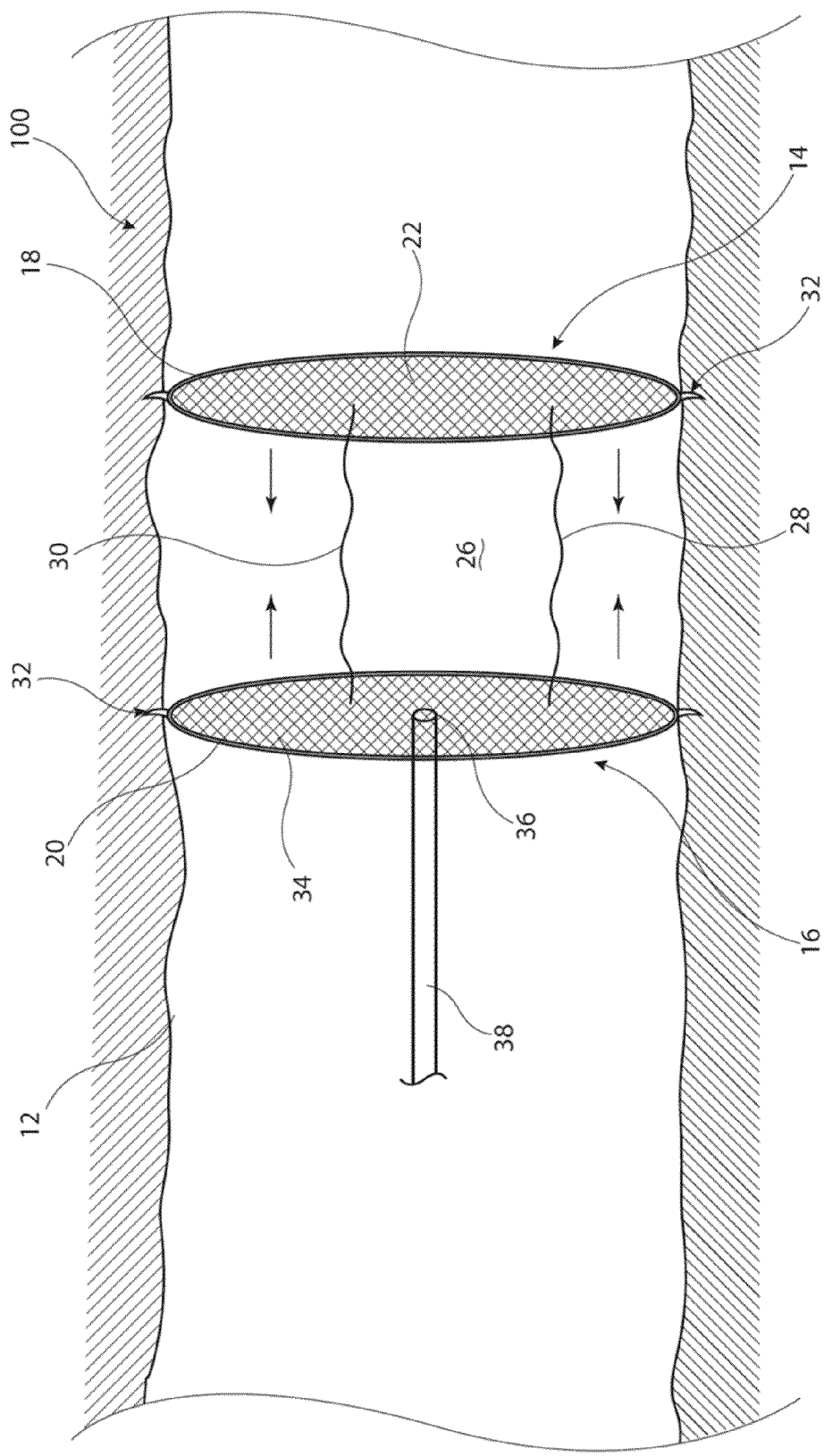
FIG. 2 is a schematic view in side elevation of another embodiment of occluder.

Another embodiment of occluder 100 is shown in FIG. 2, which has characteristic elements very similar to those of the embodiment of FIG. 1. As can be seen, the occluder 100 includes first and second baffle members 14, 16 coupled to one another by spacer elements 28, 30. Each baffle member 14, 16 includes an expansion device 18, 20 and a membrane extending across the expandable elements. In this embodiment, the expansion device 18 includes a membrane 22 equivalent to that of the embodiment of FIG. 1. On the other hand, the expansion device 20 has extending thereacross a membrane 34 which includes an aperture 36 for receiving the distal end of a delivery catheter 38.

The membranes 22, 34 may be made of the same materials as those disclosed above.

The delivery catheter 38 is preferably a separate component from the occluder 100 and therefore is removable from a patient after the deployment of the occluder 100. The delivery catheter 38 is, in this embodiment, configured to deliver into the chamber 26 between the baffle members 14, 16 a thrombogenic agent for promoting clotting of blood located within the chamber 26. As explained below, the delivery of a thrombogenic agent can provide more rapid generation of a thrombus within the chamber 26 and thus enhanced occlusion, particularly in cases where the occluder is deployed in a high pressure vessel.

Figure 3:
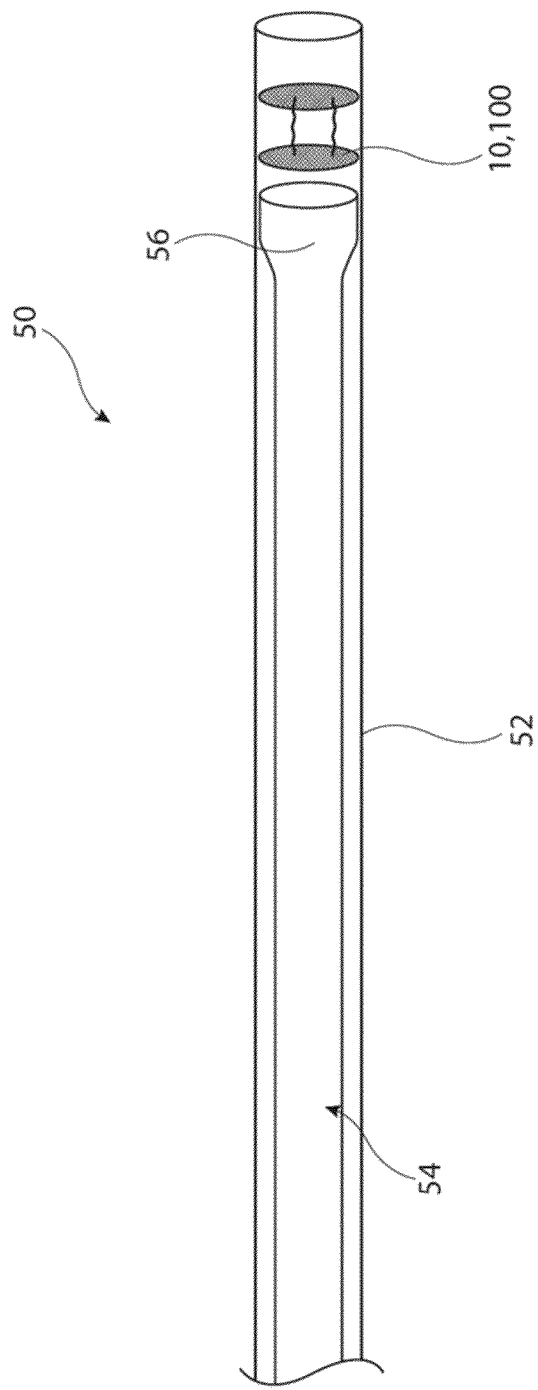
FIG. 3 is a schematic view in side elevation of an embodiment of introducer assembly incorporating an occluder as taught herein.

Referring now to FIG. 3, there is shown an example of the principal components of a deployment assembly for deploying the occluder 10, 100 taught herein. The assembly 50 includes a catheter or sheath 52 of elongate and flexible form, having a structure equivalent to that of known introducer assembly catheters and sheaths. The assembly 50 also includes, in this embodiment, a pusher element 54, again of elongate form which includes a pusher head 56 disposed in abutment with the occluder 10, 100, the latter held in radially compressed form within the sheath 50.

The occluder 10, 100 is deployed by pushing the compressed occluder out of the sheath by means of the pusher element 54, in a manner which will be apparent to the person skilled in the art. The occluder 10, 100 will automatically expand once released from the constraint of the sheath 50, until the expansion devices 18, 20 come into abutment with the walls of the vessel 12.

The deployment of the occluder 10, 100 taught herein by means of the deployment assembly 50 can generally be effected as follows.

Once the distal end of the sheath 52 has been located at the site in the patient's vessel to be occluded, the pusher rod 54 and sheath 52 are actuated to push the first baffle member 14 out of the sheath 52, which will then expand by means of its expansion device 18 so as to expand to the width of the vessel 12. The barbs 32 will embed into the walls of the vessel 12, thereby to hold the first baffle member 14 in position. Further actuation of the pusher rod 54 and sheath 52 will then release the second baffle member 60 from the sheath 52, which in turn will expand to the diameter of the vessel 12 with its barbs 32 becoming embedded within the walls of the vessel. The spacer elements 28, 30 will hold the first and second baffle members 14, 16 spaced apart as shown in FIGS. 1 and 2, thereby to form the chamber 26 between the baffle members. It is envisaged in some embodiments that the spacer elements 28, 30 can be expanded longitudinally during the deployment process, so as to produce a contraction force, depicted by the arrows in FIGS. 1 and 2. Such longitudinal expansion can be achieved by pulling back the assembly 50 once the first baffle member 14 has been deployed in the vessel and is held in position by its barbs 32. The resiliency of the spacer elements 28, 30 will produce a return force urging the baffle members, 14, 16 towards one another, which can have a stabilizing effect on the occluder 10, 100 and in particular in terms of holding it in position within the vessel 12.

In the case of the embodiment of FIG. 2, once the second baffle member 16 has been expanded to its deployed diameter, the sheath 52 can then be pushed into the aperture 36 in the membrane 34 so as to couple into the chamber 26. Once this has been achieved, a thrombogenic agent can be injected into the chamber 26 through the lumen of the sheath 52, thereby to promote clotting of blood within the chamber 26. The sheath 52 can then be withdrawn from the occluder 100 and from patient. The aperture 36 in the membrane 34 will play no further part in the operation of the occluder 100.

The aperture 36 need not necessarily be closed given that the occluder 100 will in any event occlude the vessel. It is envisaged, though, that there may be provided a mass of thrombogenic fibers at the aperture 36 to promote coagulation of blood at the aperture 36 and thereby create a plug to seal the aperture 36.

In other embodiments, the assembly 50 may include a catheter distinct from the outer sheath 52 for injecting thrombogenic agent into the chamber 26, in which case the delivery catheter can have a smaller diameter than the sheath 52 and the aperture 36 in the membrane 34 may likewise be of smaller diameter. Such an additional catheter could be fed through the sheath 52 after deployment of the occluder 10, 100 and can likewise be included within the assembly 50 with the occluder 10, 100, for example within a suitable lumen in the pusher element 54. In this case, the delivery catheter could be pre-positioned within the aperture 36 when the occluder 100 is disposed in the delivery sheath 52.

It is also envisaged that the occluder 10, 100 could be delivered over the wire, in which case both membranes 22 and 24/34 could be provided with small apertures therein for receiving a guide wire and/or a guide wire catheter therethrough. There may be provided at such apertures a mass of thrombogenic fibers to promote blood clotting, thereby creating a plug closing the apertures. In such embodiments, a guide wire catheter can also be used as the catheter for delivery of thrombogenic agent into the chamber 26 formed between the baffle members 14, 16.

The embodiments described above and shown in the drawings show an occluder having two baffle members 14, 16. It is to be understood that the occluder can have more than two baffle members if desired or advantageous, with adjacent baffle members being held separated from one another by spacer elements of the type taught herein.

The occluder 10, 100 disclosed herein is able to provide a known length occlusion device and in the preferred embodiments substantially instantaneous occlusion of a body vessel. Moreover, the structure of occluder taught herein can avoid problems of recanalization of the vessel following implantation of the occluder.

It may be advantageous in some applications to provide the occluder for only a finite period within the patient, in which case at least a part of the occluder, typically the membranes 22, 24 of a biodegradable material. The entirety of the device may be made of biodegradable material, including the expansion devices 18, 20 and the spacer elements 28, 30.

All optional and preferred features and modifications of the described embodiments and dependent claims are usable in all aspects of the invention taught herein. Furthermore, the individual features of the dependent claims, as well as all optional and preferred features and modifications of the described embodiments are combinable and interchangeable with one another.

The disclosure in the abstract accompanying this application is incorporated herein by reference.

The invention claimed is:

1. A vascular occluder including:
   first and second baffle members, each baffle member including an annular expansion device and a membrane extending across the expansion device, the second baffle member being substantially impermeable to blood flow therethrough and the first baffle member being permeable to blood flow therethrough, and
   at least one spacer element disposed between the first and second baffle members to hold the first and second baffle members at a distance from one another so as to provide a chamber between the first and second baffle members;
   wherein the first baffle member includes an opening for removably receiving a delivery catheter, and
   wherein the membrane of the second baffle member is unitary across the expansion device across which it extends.

2. The vascular occluder according to claim 1, wherein the at least one spacer element is disposed at a location radially internally of the expansion members.

3. The vascular occluder according to claim 1, wherein each expansion device is a radially expandable ring.

4. The vascular occluder according to claim 3, wherein the expandable ring is a stent ring.

5. The vascular occluder according to claim 1, wherein the at least one spacer element is flexible.

6. The vascular occluder according to claim 1, wherein the at least one spacer element is a sprung structure.

7. The vascular occluder according to claim 1, wherein the at least one spacer element is disposed substantially at a radial midpoint of the occluder relative to the radius of the baffle members.

8. The vascular occluder according to claim 1, further comprising anchoring elements provided on at least one of the first and second baffle members.

9. The vascular occluder according to claim 8, wherein the anchoring elements are barbs.

10. The vascular occluder according to claim 1, wherein the first and second baffle members are compressible into the delivery catheter.

11. An assembly for occluding a body vessel including:
    a delivery catheter having a distal end; and
    a vascular occluder comprising:
        first and second baffle members, each baffle member including an annular expansion device and a membrane extending across the expansion device, one of the first and second baffle members being substantially impermeable to blood flow therethrough and the other of the first and second baffle members being permeable to blood flow therethrough, and
        at least one spacer element disposed between the first and second baffle members, the at least one spacer element being biased to hold the first and second baffle members at a distance from one another so as to provide a chamber between the first and second baffle members;
        wherein the first baffle member includes an opening for removably receiving a delivery catheter; and
        wherein the delivery catheter is configured to be coupled through the first baffle member to the chamber.

12. The assembly according to claim 11, wherein the vascular occluder is configured to be compressible into the delivery catheter.

13. The assembly according to claim 11, wherein the delivery catheter is coupled to deliver a thrombogenic agent into the chamber between the first and second baffle members.

14. The assembly according to claim 11 wherein the second baffle member is unitary across the expansion device across which it extends.

15. A vascular occluder including:
    first and second baffle members, each baffle member including an annular expansion device and a membrane extending across the expansion device, the second baffle member being substantially impermeable to blood flow therethrough and the first baffle member being permeable to blood flow therethrough, and
    at least one spacer element disposed between the first and second baffle members biased to hold the first and second baffle members at a distance from one another so as to provide a chamber between the first and second baffle members;
    wherein the first baffle member includes an opening for removably receiving a delivery catheter, and
    wherein the membrane of the second baffle member is unitary across the expansion device across which it extends.

* * * * *